US008905022B2

(12) United States Patent
Parkes et al.

(10) Patent No.: US 8,905,022 B2
(45) Date of Patent: Dec. 9, 2014

(54) DRY POWDER INHALERS

(75) Inventors: Philip Carl Parkes, Chippenham (GB); Steven Graham Williams, Chippenham (GB)

(73) Assignee: Innovata Biomed Limited, Edinburgh (GB)

( * ) Notice: Subject to any disclaimer, the term of this patent is extended or adjusted under 35 U.S.C. 154(b) by 474 days.

(21) Appl. No.: 13/384,182

(22) PCT Filed: Jul. 16, 2010

(86) PCT No.: PCT/GB2010/051167
§ 371 (c)(1), (2), (4) Date: Jan. 13, 2012

(87) PCT Pub. No.: WO2011/007181
PCT Pub. Date: Jan. 20, 2011

(65) Prior Publication Data
US 2012/0111328 A1 May 10, 2012

(30) Foreign Application Priority Data
Jul. 16, 2009 (GB) .................................. 0912373.8

(51) Int. Cl.
*A61M 15/00* (2006.01)
(52) U.S. Cl.
CPC ....... *A61M 15/0065* (2013.01); *A61M 15/0003* (2014.02); *A61M 2202/064* (2013.01)
USPC ............. 128/203.15; 128/203.12; 128/200.24
(58) Field of Classification Search
CPC .......... A61M 15/001; A61M 15/0003; A61M 15/0065; A61M 2202/064
USPC ............. 128/200.14, 200.17, 200.19, 203.12, 128/203.15, 203.19, 200.23, 200.24; 222/129, 424, 425, 426, 431, 452
See application file for complete search history.

(56) References Cited

U.S. PATENT DOCUMENTS 7,854,226 B2 12/2010 Pinon et al.
8,205,611 B2 6/2012 Olsson et al.
(Continued)

FOREIGN PATENT DOCUMENTS

CN 1889991 A 1/2007
CN 101455870 6/2009
(Continued)

OTHER PUBLICATIONS

Great Britain Search Report for GB0912373.8 dated Nov. 24, 2009.
(Continued)

*Primary Examiner* — Tan-Uyen T Ho
*Assistant Examiner* — Elliot S Ruddie
(74) *Attorney, Agent, or Firm* — LeClairRyan, a Professional Corporation

(57) ABSTRACT

A dry powder inhaler (1) is disclosed comprising first and second medicament reservoirs (2, 2*a*) and respective rotatable first and second metering members (5, 5*a*), which are urged into sealing engagement with the respective medicament reservoir (2, 2*a*) by a compression spring (8) located between the metering members (5, 5*a*). The inhaler (1) includes an actuator by which the first and second metering members (5, 5*a*) are rotated in unison from a metering position to a dispensing position. The actuator acts upon the first and second metering members (5, 5*a*) via a wheel (9) mounted between the first and second metering members (5, 5*a*). The first and second metering members (5, 5*a*) are provided with sockets (51) that receive the respective ends of the compression spring (8). The sockets (51) have extensions (52) that project into an axial bushing (92) of the wheel (9), the bushing (92) being provided on its internal surface with formations (94*a*, 94*b*, 94*c*, 94*d*) that engage the extensions (52) to cause the metering members (5,5*a*) to rotate when the wheel (9) is rotated.

12 Claims, 10 Drawing Sheets

(56) References Cited

U.S. PATENT DOCUMENTS

2003/0116157 A1* 6/2003 Braithwaite et al. ..... 128/203.15
2010/0288277 A1* 11/2010 Gordon et al. ........... 128/203.15

FOREIGN PATENT DOCUMENTS

| WO | 00/74754 | A2 | 12/2000 |
| WO | 00/74754 | A3 | 12/2000 |
| WO | 01/17595 | A1 | 3/2001 |
| WO | 01/31578 | A1 | 5/2001 |
| WO | 01/39823 | A1 | 6/2001 |
| WO | 2009/087404 | A1 | 7/2009 |
| WO | 2009/087407 | A1 | 7/2009 |

OTHER PUBLICATIONS

International Search Report for PCT/GB2010/051167 dated Apr. 10, 2010.

Written Opinion for corresponding International Application No. PCT/GB2010/051167 (Jan. 17, 2012).

* cited by examiner

DRY POWDER INHALERS

CROSS-REFERENCE TO RELATED APPLICATIONS

This application is a national stage application under 35 U.S.C. §371 from PCT Application No. PCT/GB2010/051167, filed Jul. 16, 2010, which claims the priority benefit of United Kingdom Application No. 0912373.8, filed Jul. 16, 2009, which are hereby incorporated by reference in their entirety.

BACKGROUND OF THE INVENTION

This invention relates to improvements in or relating to dry powder inhalers, in particular dry powder inhalers of the type that comprise first and second medicament reservoirs that hold bulk quantities of two different medicaments, and which have associated therewith respective rotatable first and second metering members by which doses of the two medicaments are simultaneously dispensed for simultaneous inhalation by a patient.

Dry powder inhalers of the type with which the invention is concerned are disclosed in International patent applications WO-A-01/39823, WO-A-2005/102429 and WO-A-2005/102430. In the inhalers disclosed in those documents, each medicament reservoir is associated with a rotatable metering member, typically of frustoconical form, the surface of which is provided with depressions that constitute cups for the volumetric metering of a dose of medicament. The metering member is pressed into close engagement with an opening in the reservoir by a compression spring and a lower part of the reservoir assembly constitutes a support for the metering member, within which the metering member rotates. The two metering members rotate about a common axis, the compression spring being mounted between them and urging them outwardly into engagement with the respective supports. An actuator, eg a manually operated push button, causes the metering members to rotate in unison and to transfer doses of the two medicaments from the reservoirs to a position from which the doses can be inhaled by the patient.

In a device of the type described above, it is important that the seal between the metering members and their respective support structures should be as tight as possible, to minimise the possibility of ingress of moisture into the medicament reservoirs, since moisture may cause degradation of the medicaments, and/or faulty operation of the dosing mechanism, and/or agglomeration of the medicament powders, all of which (as is well known) have adverse therapeutic consequences for the patient. It is also important that the metering members should be coupled together in such a way that they operate in unison, so that medicaments that are intended to be administered together are indeed so administered. Despite these requirements, it is also important that the device should be easily and reliably manufacturable.

There have now been devised improvements to dry powder inhalers of the type generally described above that address the above mentioned requirements and/or other disadvantages of the prior art.

SUMMARY OF THE INVENTION

According to the invention, there is provided a dry powder inhaler of the type that comprises first and second medicament reservoirs, said first and second medicament reservoirs having associated therewith respective rotatable first and second metering members, the first and second metering members being mounted for rotation about a common axis and urged into sealing engagement with the respective medicament reservoir by a compression spring located between the first and second metering members and mounted about said axis, and the inhaler including an actuator by which the first and second metering members are rotated in unison from a metering position, at which the first and second metering members are charged with doses of medicament from the associated reservoirs, to a dispensing position, at which said doses are or can be discharged from the first and second metering members, characterised in that the actuator acts upon the first and second metering members via a wheel mounted between the first and second metering members for rotation about said axis, the first and second metering members being provided with sockets that receive the respective ends of the compression spring, the sockets having extensions that project into an axial bushing of the wheel, the bushing being provided on its internal surface with formations that engage the extensions to cause the metering members to rotate when the wheel is rotated.

The inhaler according to the invention is advantageous in that the manner in which the metering members engage the wheel, and the manner in which the compression spring is captivated between the sockets and within the bushing of the wheel, result in the compressive forces of the spring being efficiently applied to the metering members, and hence to effective sealing of the metering members against their supports. The arrangement is also relatively easy to assemble and facilitates correct orientation and alignment of the metering members. The metering members are also coupled together by the wheel, so that simultaneous rotation of the metering members is ensured.

Each metering member is preferably provided with two extensions. Where the metering member has two extensions, the extensions are preferably at diametrically opposed sides of the socket.

The extensions are preferably arcuate in cross-section, having a radius corresponding to that of the socket from which they extend, and being concentric with the internal bore of the bushing, so that the extensions are closely received within the bushing.

The metering members may be arranged with their extensions all parallel to the axis of rotation, with the extensions of one metering member disposed at 90° to the extensions of the other.

The extensions of the two metering members may overlap, so that the sockets, extensions and bushing constitute a substantially complete enclosure for the spring. Such an arrangement will prevent substantial lateral movement or buckling of the spring, and so may lead to an improved seal of the metering members against the reservoirs, with corresponding improvements in performance of the inhaler.

The formations on the internal surface of the bushing that enable the bushing to engage the extensions are most preferably ribs or splines that extend parallel to the axis of rotation. The spacing between such ribs or splines is preferably such that the extensions are closely received between them. The ribs or splines may be arranged such their ends are offset from each other, such that at each end of the bushing two of the spaces between the ribs or splines is greater than the other two spaces between the ribs or splines.

The wheel is preferably provided with formations that enable the actuator to bring about rotation of the wheel. Typically, the wheel will be provided with ratchet formations that are engaged by a reciprocating push-rod.

An embodiment of the invention will now be described, by way of illustration only, with reference to the accompanying drawings, in which

DETAILED DESCRIPTION OF THE INVENTION

Figure 1:
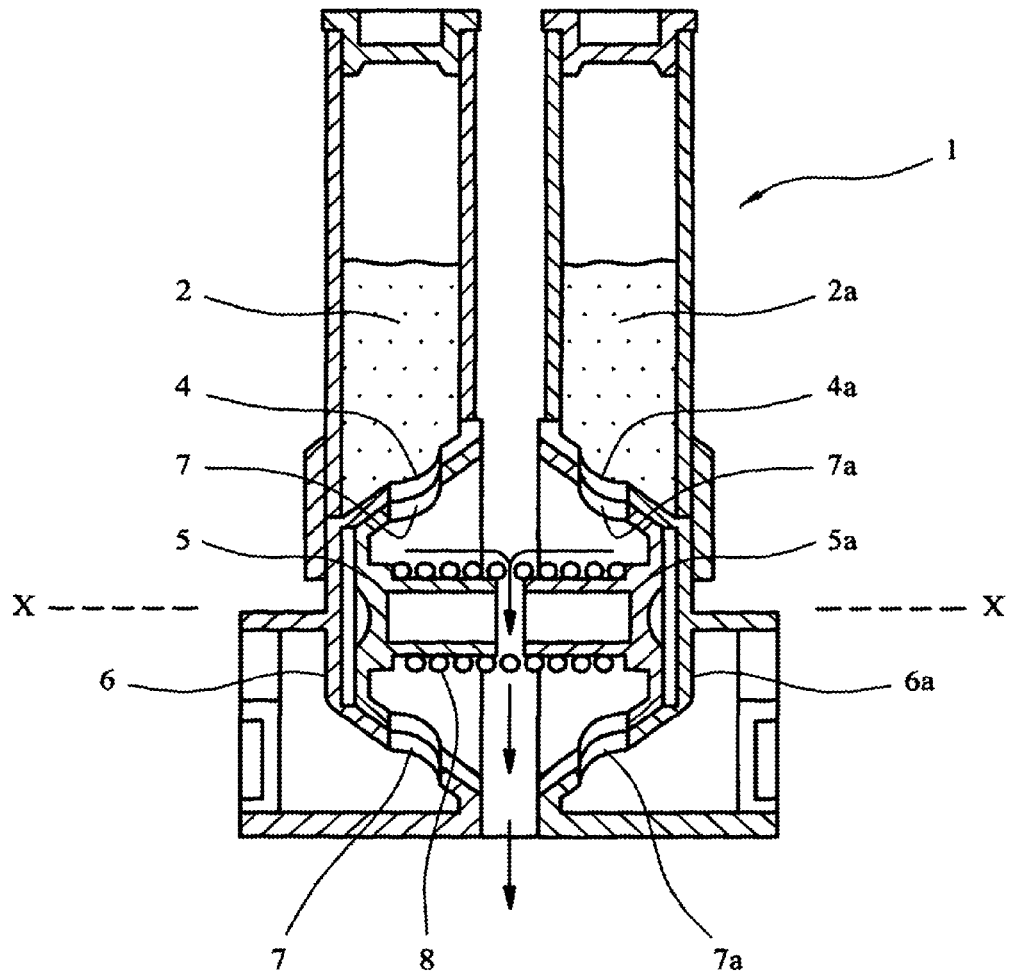
FIG. 1 is a schematic sectional view of a dry powder inhaler of the general type with which the present invention is concerned.
Figure 2:
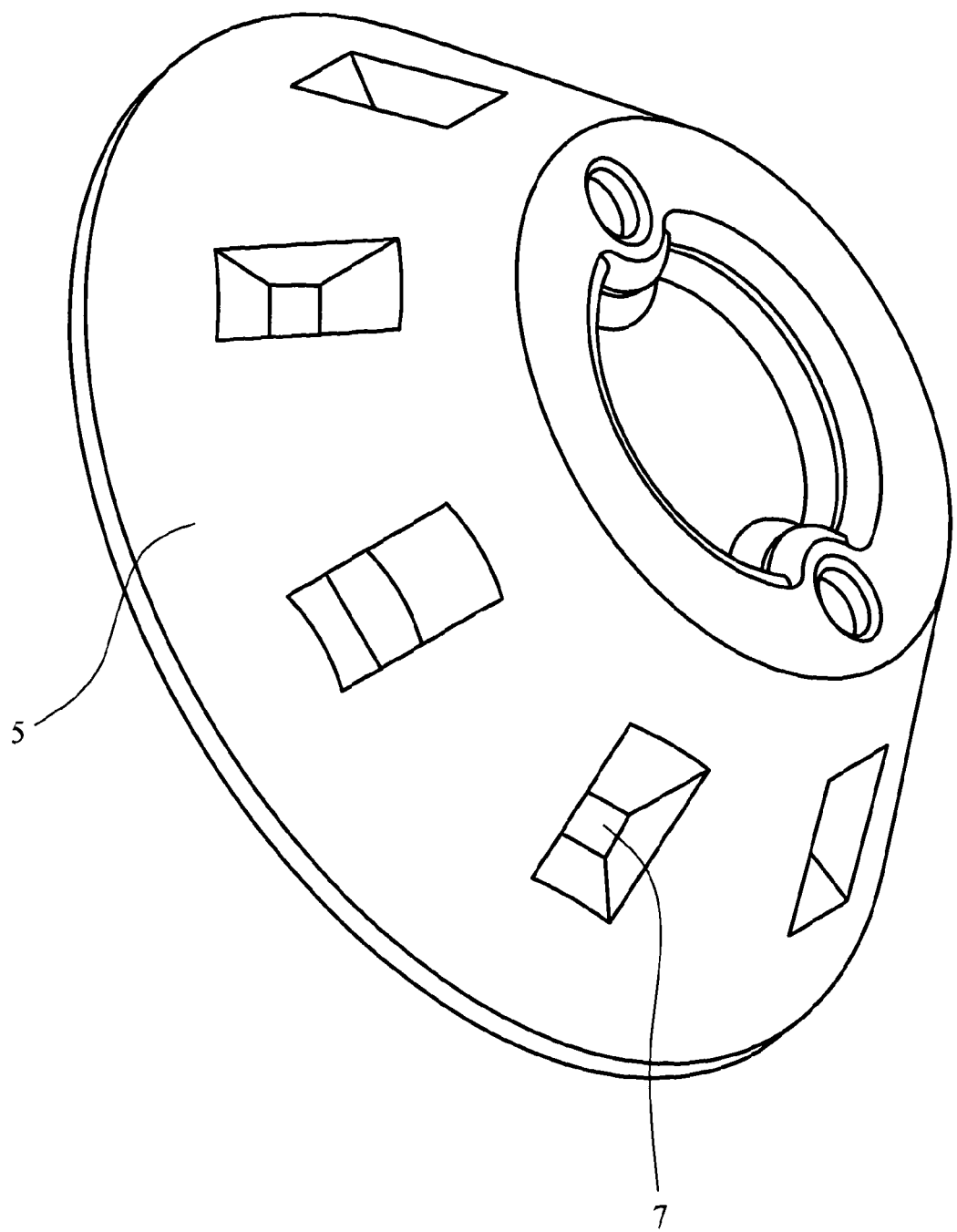
FIG. 2 is a perspective view, from above, of a metering member forming part of a dry powder inhaler according to the invention.

Referring first to FIG. 1, a dry powder inhaler is generally designated 1 and is for the simultaneous administration of unit doses of two different powdered medicaments.

The inhaler 1 comprises first and second reservoirs 2,2a that contain bulk quantities of the two medicaments and are arranged side by side and, in normal use of the inhaler 1, substantially vertically.

The reservoir 2 has an opening 4 in its base, from which powdered medicament is discharged from the reservoir 2 under the influence of gravity. A frustoconical metering member 5 is positioned beneath the reservoir 2, such that the surface of the metering member 5 closely abuts the underside of the reservoir 2 so as to close off the opening 4. The reservoir 2 is formed integrally with a frustoconical support 6 within which the metering member 5 is received. The metering member 5 has a number of depressions 7 formed in its surface. Two such depressions 7 are evident in FIG. 1. The depressions 7 serve as metering cups by which a dose of medicament is volumetrically dispensed from the reservoir 2. When a depression 7 is in registration with the opening 4, the depression 7 fills with a dose of powdered medicament. Rotation of the metering member 5 then transports that dose to a position from which it can be inhaled by the patient, and at the same time brings another depression 7 into registration with the opening 4.

The other reservoir 2a and associated components are identical to those described in the preceding paragraph, save that they are disposed in an arrangement that is the mirror image of that depicted for the first reservoir 2. Components associated with the second reservoir 2a that correspond to components 4,5,6,7 associated with the first reservoir 2 are denoted 4a, 5a, 6a, 7a.

The two metering members are capable of rotating about a common axis, indicated in FIG. 1 by the broken line X-X.

A compression spring 8 is mounted between the metering members 5,5a, and urges the metering members 5,5a outwards, into engagement with the respective supports 6,6a.

The general manner of operation of the inhaler 1 is that depressions 7,7a that are in registration with the openings 4,4a are charged with doses of the respective medicaments. When it is desired to administer these doses, the patient causes the metering members 5,5a to rotate such that the doses are transported to a position from which they can be inhaled. At the same time, empty depressions 7,7a are brought into registration with the openings 4,4a. Rotation of the metering members 5,5a is most commonly brought about by a ratchet-type mechanism operated by a push button or the like.

The metering member 5 of an inhaler according to the invention is shown in detail in FIGS. 2 to 5. As can readily be seen, the metering member 5 has a generally frustoconical form. The conical part of the outer surface of the metering member 5 is formed with a plurality of (in the illustrated embodiment, eight) depressions (metering cups) 7, that are spaced equiangularly around the metering member 5.

Figure 3:
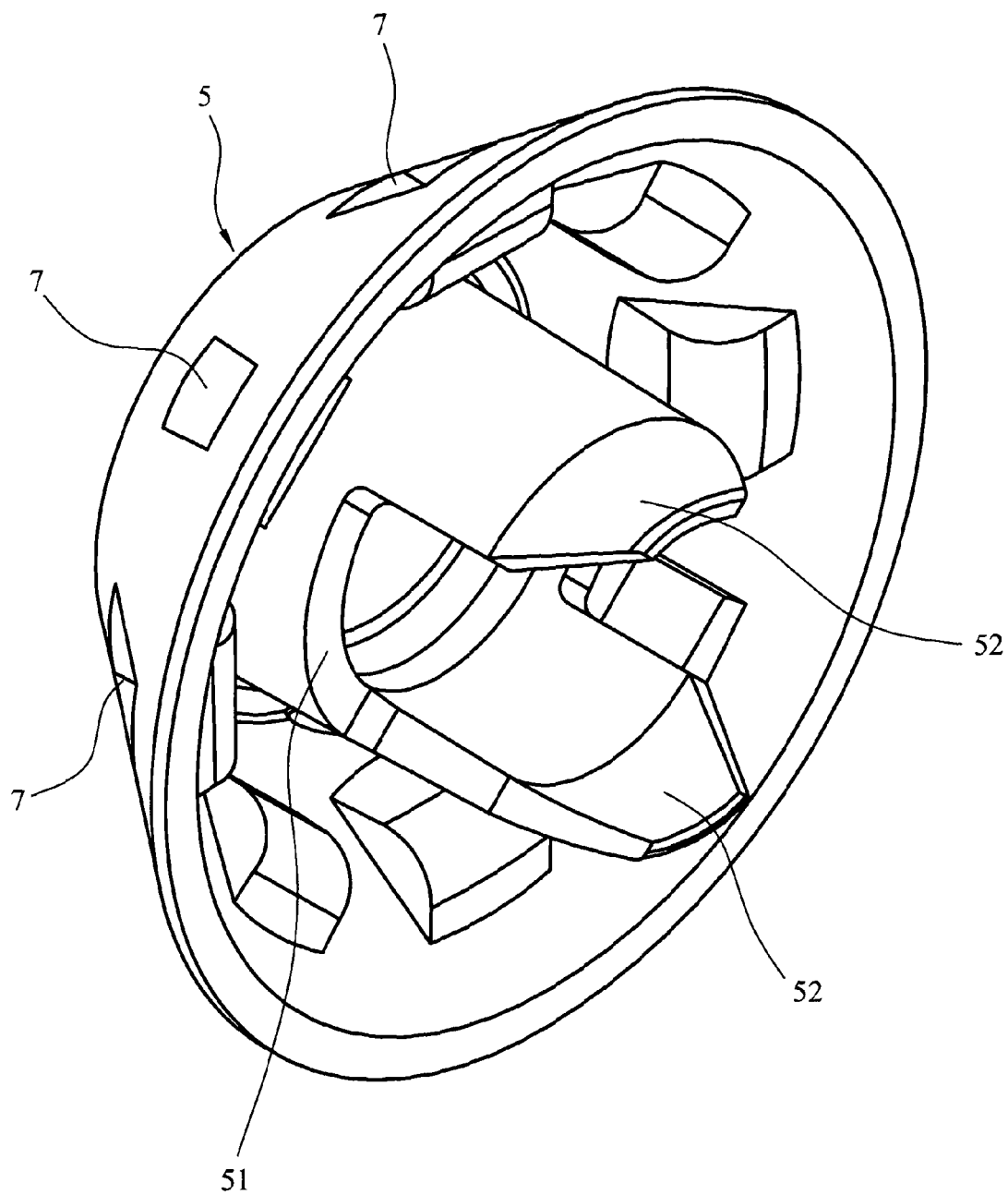
FIG. 3 is a perspective view, from below, of the metering member of FIG. 2.
Figure 4:
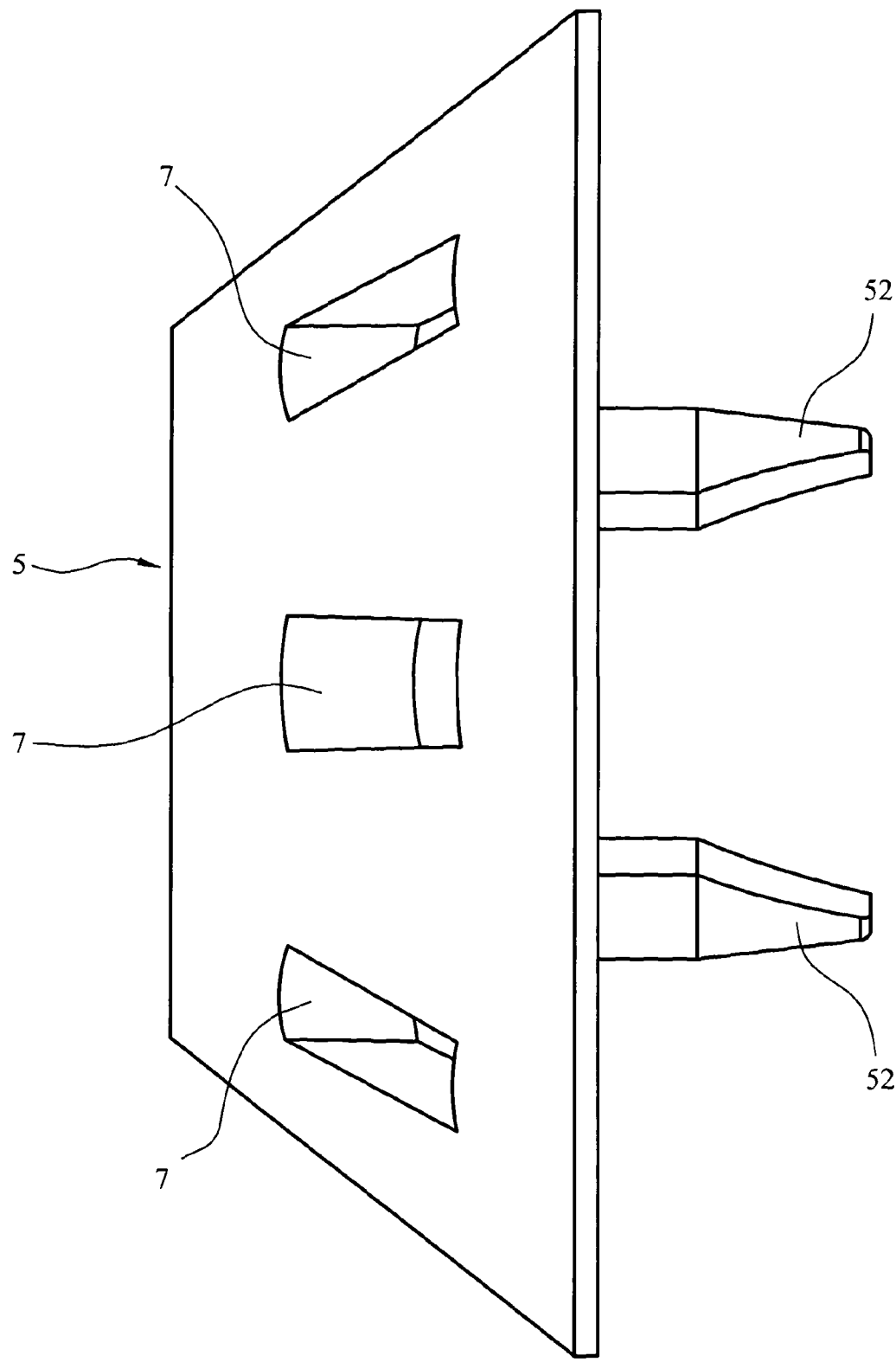
FIG. 4 is a side view of the metering member of FIGS. 2 and 3.
Figure 5:
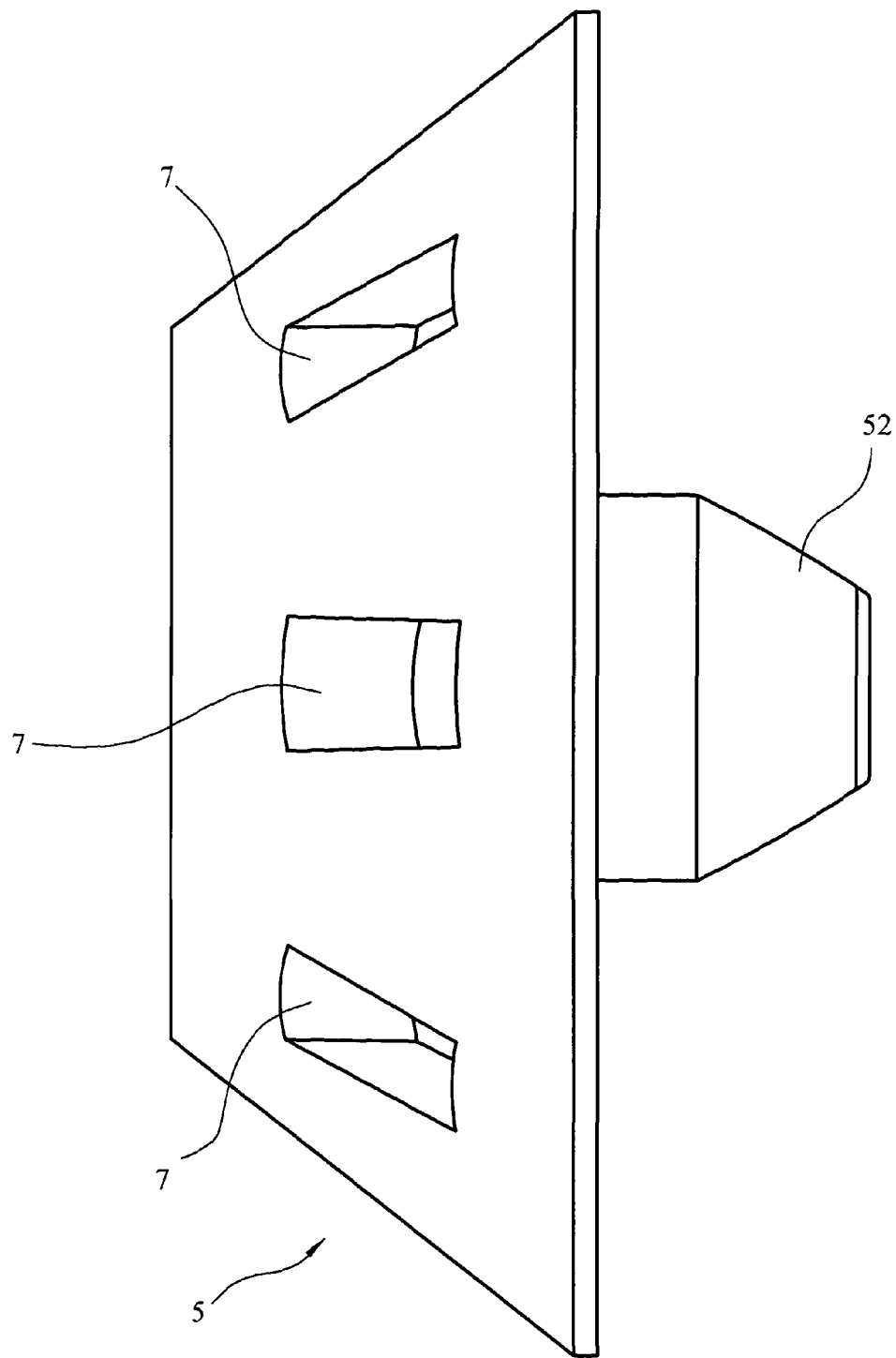
FIG. 5 is a second side view, orthogonal to FIG. 4, of the metering member.

The features of the metering member 5 that are specific to the present invention are visible in FIGS. 3 to 5. These are that the underside of the metering member 5, which is hollow, is formed with a circular socket 51, from which a pair of diametrically opposed extensions 52 project. The internal diameter of the socket 51 is such that it closely receives the compression spring 8, as described in more detail below. The extensions 52 project beyond the frustoconical part of the metering member 5, as can clearly be seen in FIGS. 4 and 5.

The extensions 52 are of arcuate cross-section, and are in effect extensions of the circular wall of the socket 51. Each projection 52 has a width that corresponds to approximately 90° of the circumference of the socket 51. The tips of the projections 52 are tapered.

Figure 6:
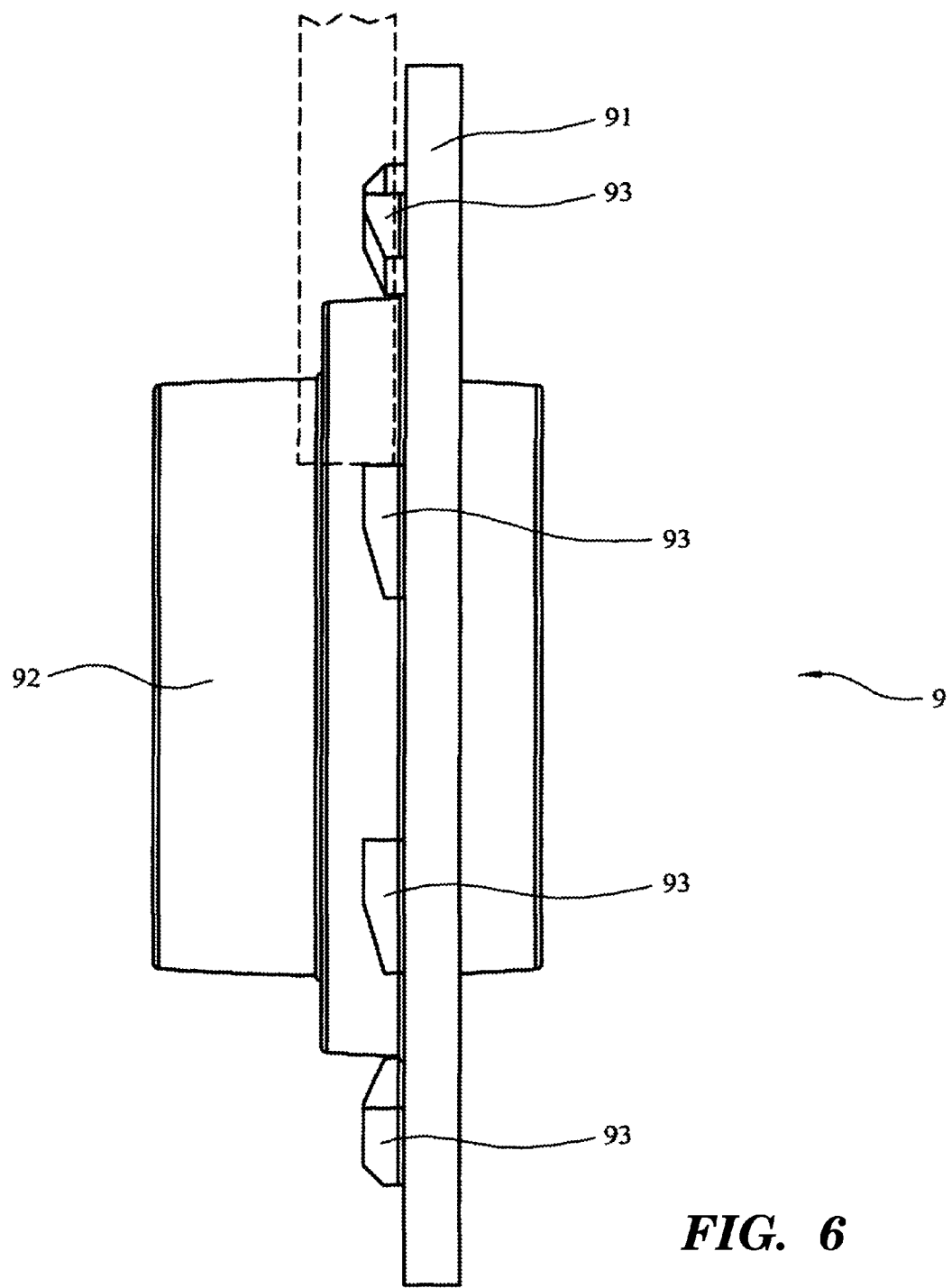
FIG. 6 is a side view of a wheel that engages a pair of metering members of the form shown in FIGS. 2 to 5 in the dry powder inhaler of the invention.
Figure 7:
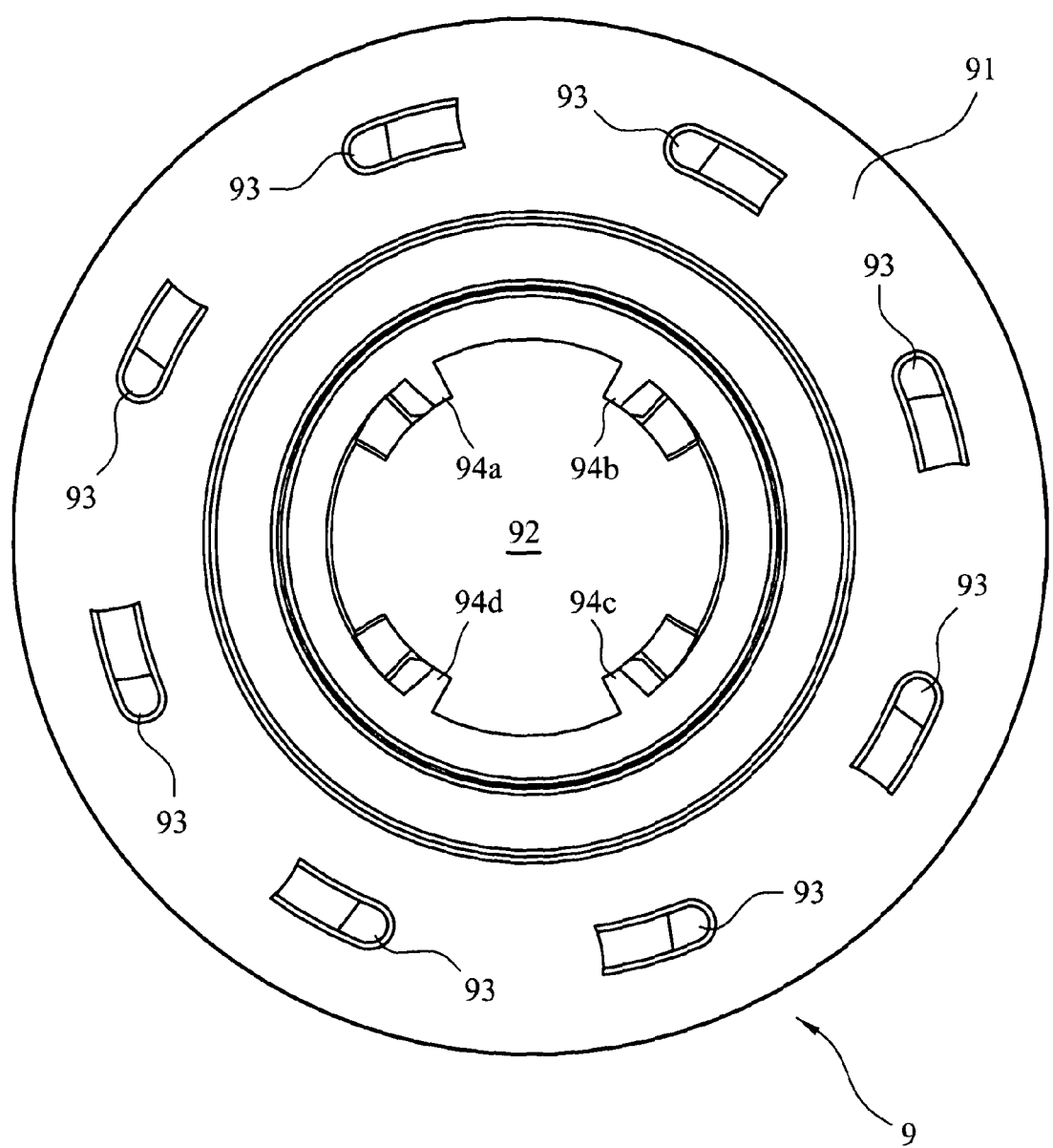
FIG. 7 is a plan view of the wheel of FIG. 6.
Figure 8:
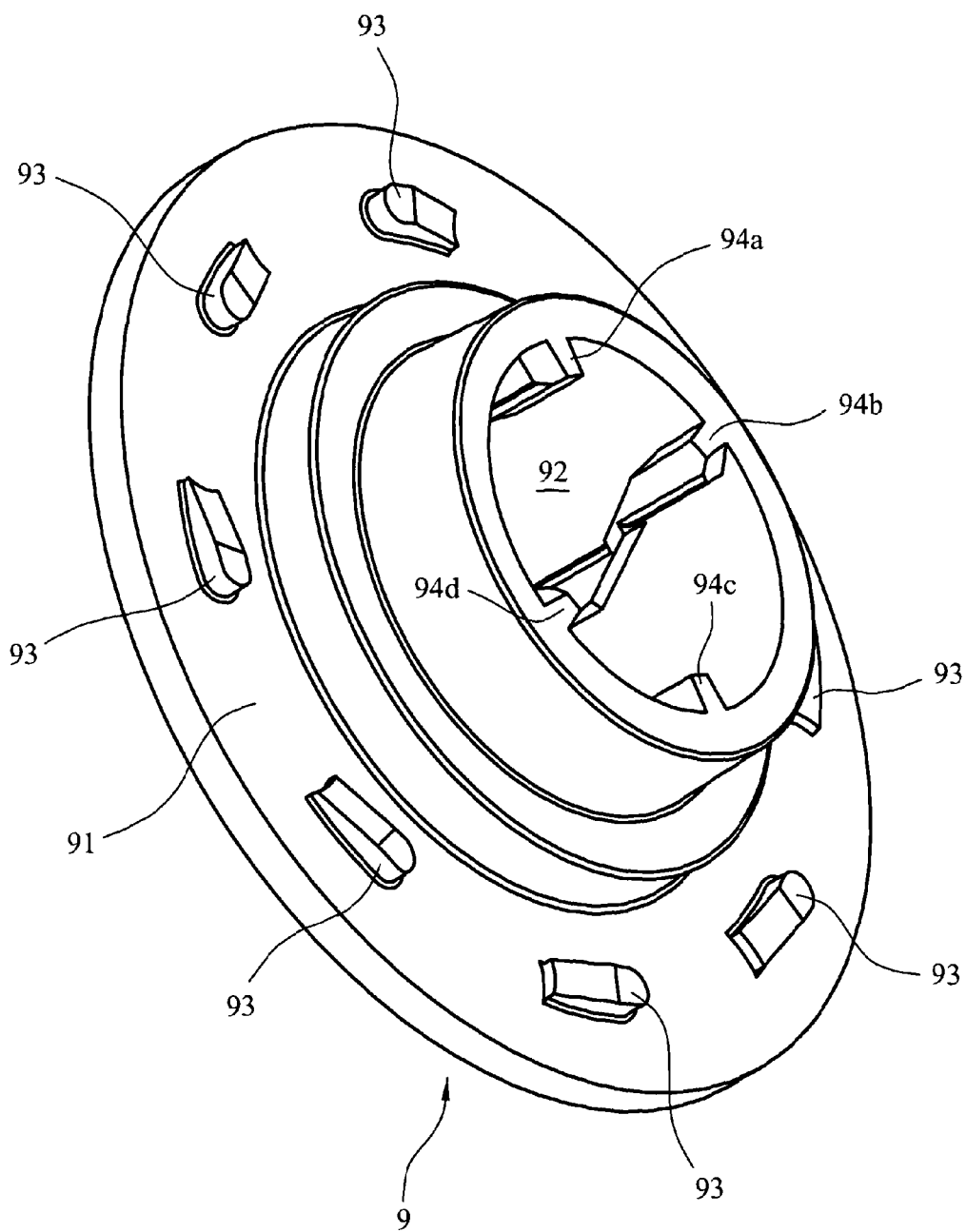
FIG. 8 is a perspective view of the wheel of FIGS. 6 and 7.

FIGS. 6 to 8 show a wheel 9 that couples the operation of an actuator (eg a push button operated by the user of the inhaler 1) to the metering members 5,5a. The wheel 9 comprises a disc 91 with a central cylindrical bushing 92. One face of the disc 91 is formed with a plurality of (in the illustrated embodiment, eight) ratchet formations 93. Each ratchet formation 93 has a flat top and a ramped lower part. The manner in which the wheel 9 is rotated by the actuator is not critical to the present invention, but can be summarised as follows. A reciprocating push-rod (indicated in broken lines in FIG. 6) bears against one of the ratchet formations 93. Depression of the push-rod against the action of a spring (not shown) causes the wheel 9 to rotate through 45°. The push-rod then returns to its rest position, riding over the ramped lower part of the next ratchet formation 93 and coming to rest adjacent to the flat top of that ratchet formation 93, ready for the next actuation of the inhaler 1.

As can be seen in FIGS. 7 and 8, the internal surface of the bushing 92 is formed with four splines 94a-d that extend along the full length of the bushing 92, generally parallel to the longitudinal axis of the bushing. The splines 94a-d have a dog-leg or cranked configuration. The effect of this is that, at the end of the bushing 92 that is shown in FIG. 7, the ends of the splines 94a, 94b are separated by an angle of less than 90° and the same is true of the ends of the splines 94c, 94d. The angle between the pairs of splines 94b, 94c and between the splines 94d, 94a, on the other hand, is slightly greater than 90°. At the other end of the bushing 92, it is the pairs of splines 94b, 94c and 94a, 94d that are separated by less than 90°.

Figure 9:
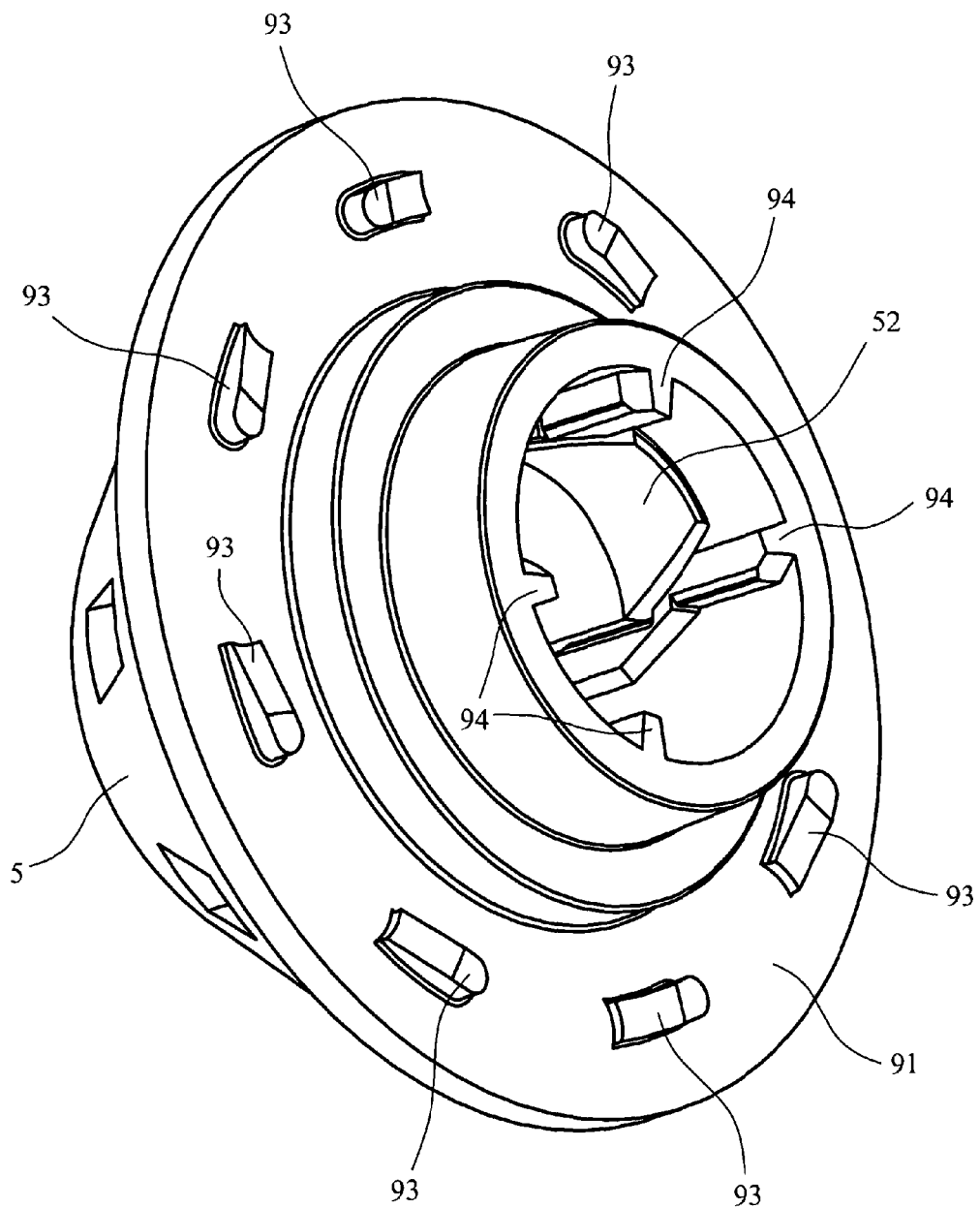
FIG. 9 is a view similar to FIG. 8, but with a metering member engaged with the wheel.

FIG. 9 shows the wheel 9 with one metering member 5 engaged with it. The extensions 52 of that metering member 5 are received between the pairs of splines 94 that have a separation of greater than 90° (the width of the extensions 52 is too great for them to be received between the other pairs of splines 94). The tapered tips of the extensions 52, however, are received between the less widely spaced parts of the splines 94 at the other end of the bushing 92. In a similar manner, a second metering member 5a can be engaged with the wheel 9 from the other side, with the extensions 52 of that metering member 5a being received in the spaces between splines 94 that are not occupied by the extensions of the first metering member 5.

Figure 10:
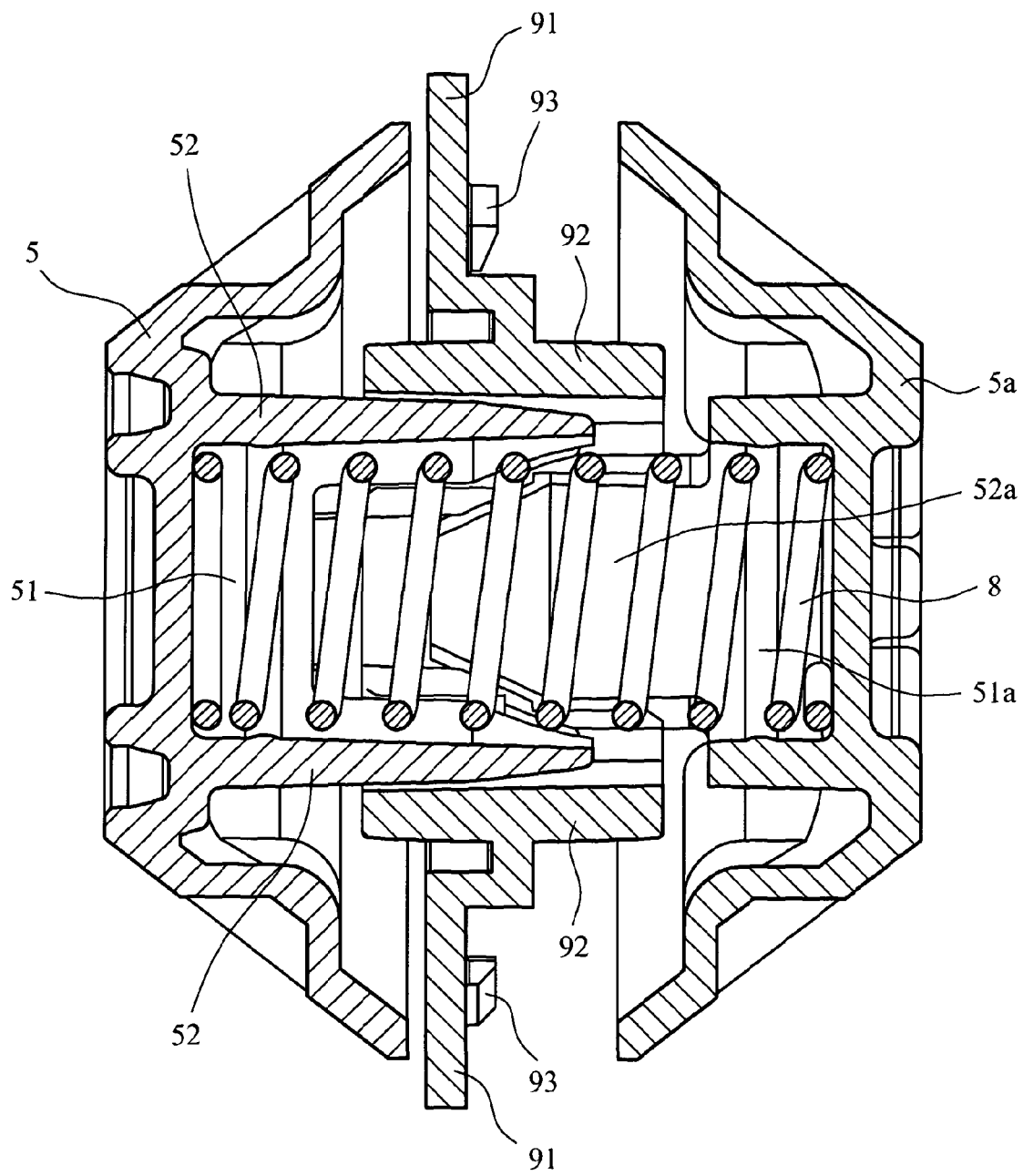
FIG. 10 is a sectional view of an assembly of two metering members engaged with the wheel, and with a compression spring captivated within the assembly.

The completed assembly of wheel 9 and two metering members 5,5a, with a compression spring 8 captivated between them, is shown in section in FIG. 10. The ends of the compression spring 8 are received within the circular sockets 51,51a of the two metering members 5,5a. Those two sockets 51,51a, together with the extensions 52,52a, form a substantially complete enclosure for the spring 8, permitting little or no lateral movement of the spring 8. The metering members 5,5a are effectively coupled to the wheel 9, so that rotation of the wheel 9 causes rotation of both metering members 5,5a in unison. Nonetheless, because the metering members 5,5a are not fixed to the wheel 9, movement of the metering members 5,5a along their axis of rotation is restrained only by the supports 6,6a within which the metering members 5,5a are received. The metering members 5,5a are therefore pressed into close engagement with the supports 6,6a by the action of the compression spring 8.

The invention claimed is:

1. A dry powder inhaler of the type that comprises first and second medicament reservoirs, said first and second medicament reservoirs having associated therewith respective rotatable first and second metering members, the first and second metering members being mounted for rotation about a common axis and urged into sealing engagement with the respective medicament reservoir by a compression spring located between the first and second metering members and mounted about said axis, and the inhaler including an actuator by which the first and second metering members are rotated in unison from a metering position, at which the first and second metering members are charged with doses of medicament from the associated reservoirs, to a dispensing position, at which said doses are or can be discharged from the first and second metering members, characterised in that the actuator acts upon the first and second metering members via a wheel mounted between the first and second metering members for rotation about said axis, the first and second metering members being provided with sockets that receive the respective ends of the compression spring, the sockets having extensions that project into an axial bushing of the wheel, the bushing being provided on its internal surface with formations that engage the extensions to cause the metering members to rotate when the wheel is rotated.

2. A dry powder inhaler as claimed in claim 1, wherein each metering member is provided with two extensions.

3. A dry powder inhaler as claimed in claim 2, wherein the extensions are at diametrically opposed sides of the socket.

4. A dry powder inhaler as claimed in claim 1, wherein the extensions are arcuate in cross-section, having a radius corresponding to that of the socket from which they extend, and being concentric with the internal bore of the bushing, so that the extensions are closely received within the bushing.

5. A dry powder inhaler as claimed in claim 1, wherein the metering members are arranged with their extensions all parallel to the axis of rotation, with the extensions of one metering member disposed at 90° to the extensions of the other.

6. A dry powder inhaler as claimed in claim 1, wherein the extensions of the two metering members overlap, so that the sockets, extensions and bushing constitute a substantially complete enclosure for the spring.

7. A dry powder inhaler as claimed in claim 1, wherein the formations on the internal surface of the bushing that enable the bushing to engage the extensions are ribs or splines that extend parallel to the axis of rotation.

8. A dry powder inhaler as claimed in claim 7, wherein the spacing between such ribs or splines is such that the extensions are closely received between them.

9. A dry powder inhaler as claimed in claim 8, wherein the ribs or splines are arranged with their ends are offset from each other, such that at each end of the bushing two of the spaces between the ribs or splines is greater than the other two spaces between the ribs or splines.

10. A dry powder inhaler as claimed in claim 9, wherein the ribs or splines have a dog-leg or cranked configuration.

11. A dry powder inhaler as claimed in claim 1, wherein the wheel is provided with formations that enable the actuator to bring about rotation of the wheel.

12. A dry powder inhaler as claimed in claim 11, wherein the wheel is provided with ratchet formations that are engaged by a reciprocating push-rod.

* * * * *